United States Patent
Fontius

(10) Patent No.: US 8,903,143 B2
(45) Date of Patent: Dec. 2, 2014

(54) METHOD FOR EVALUATING AT LEAST ONE IMAGE DATA RECORD

(75) Inventor: Jörg Ulrich Fontius, Neunkirchen A. Brand (DE)

(73) Assignee: Siemens Aktiengesellschaft, Munich (DE)

(*) Notice: Subject to any disclaimer, the term of this patent is extended or adjusted under 35 U.S.C. 154(b) by 921 days.

(21) Appl. No.: 12/585,933

(22) Filed: Sep. 29, 2009

(65) Prior Publication Data

US 2010/0080428 A1 Apr. 1, 2010

(30) Foreign Application Priority Data

Sep. 30, 2008 (DE) .......................... 10 2008 049 563

(51) Int. Cl.
- *G06K 9/00* (2006.01)
- *A61B 5/11* (2006.01)
- *G06T 7/20* (2006.01)
- *G06T 7/00* (2006.01)
- *A61B 5/00* (2006.01)

(52) U.S. Cl.
CPC .................. *A61B 5/1121* (2013.01); *G06T 7/20* (2013.01); *G06T 2207/30004* (2013.01); *A61B 5/1124* (2013.01); *A61B 5/4528* (2013.01); *G06T 7/0081* (2013.01)
USPC ........................................................ 382/128

(58) Field of Classification Search
CPC .............................. A61B 19/50; A61B 5/4528
USPC ........................................................ 382/128
See application file for complete search history.

(56) References Cited

U.S. PATENT DOCUMENTS

| | | | |
|---|---|---|---|
| 6,738,065 B1* | 5/2004 | Even-Zohar | 345/473 |
| 7,490,012 B2 | 2/2009 | Nakamura et al. | |
| 7,693,563 B2* | 4/2010 | Suresh et al. | 600/407 |
| 2005/0234354 A1* | 10/2005 | Rowlandson et al. | 600/509 |
| 2006/0100818 A1* | 5/2006 | Nakamura et al. | 702/142 |
| 2006/0161459 A9* | 7/2006 | Rosenfeld et al. | 705/3 |
| 2006/0287612 A1* | 12/2006 | Duda et al. | 600/587 |
| 2007/0093998 A1* | 4/2007 | El-Baroudi | 703/11 |
| 2009/0132217 A1 | 5/2009 | Nakamura et al. | |

(Continued)

FOREIGN PATENT DOCUMENTS

EP 1550401 A1 7/2005

OTHER PUBLICATIONS

Kang M., IEEE Proceedings of the Computer Animation 2002; Others; 2002.

(Continued)

*Primary Examiner* — Neal Sereboff
*Assistant Examiner* — Maroun Kanaan
(74) *Attorney, Agent, or Firm* — Harness, Dickey & Pierce, P.L.C.

(57) ABSTRACT

A method is disclosed for evaluating at least one image data record, in particular a magnetic resonance image data record, of a region of a patient including at least one joint. In at least one embodiment of the method, at least one image data record of the region is first of all recorded, the image data record is segmented with respect to at least one mechanically relevant component of the joint in order to determine segmentation information, a patient movement model is generated on the basis of the segmentation information and/or the patient movement model is selected from a database of movement models, and joint information relating to the motions of the joint is determined from the patient movement model.

19 Claims, 1 Drawing Sheet

(56) References Cited

U.S. PATENT DOCUMENTS

2009/0190815 A1* 7/2009 Dam et al. .................... 382/131
2009/0274350 A1* 11/2009 Pavlovskaia et al. ......... 382/128
2009/0297012 A1* 12/2009 Brett et al. .................... 382/132

OTHER PUBLICATIONS

Gao B., et al, Journal of Biomechanics 40 (S2), S. S 156; Others; 2007.

* cited by examiner

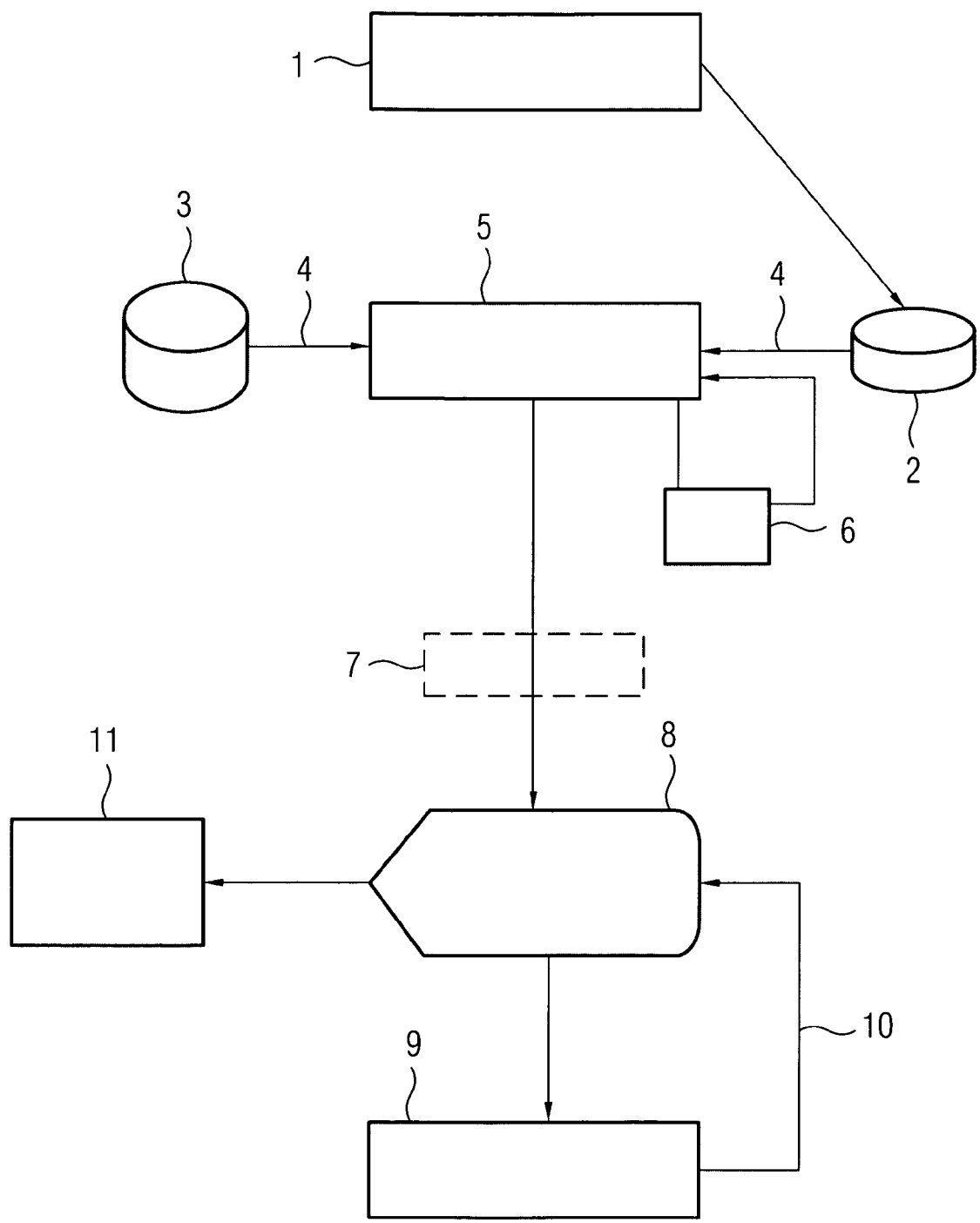

METHOD FOR EVALUATING AT LEAST ONE IMAGE DATA RECORD

PRIORITY STATEMENT

The present application hereby claims priority under 35 U.S.C. §119 on German patent application number DE 10 2008 049 563.8 filed Sep. 30, 2008, the entire contents of which are hereby incorporated herein by reference.

FIELD

At least one embodiment of the invention generally relates to a method for evaluating at least one image data record, in particular a magnetic resonance image data record, of a region of a patient comprising at least one joint.

BACKGROUND

In the case of medical diagnosis of the locomotor apparatus, in particular of one or more joints, it is known to record series of image data records which show the examined joint in a number of positions along one or more motions. The different stages of the motion can then for example be examined with respect to anomalous touches, e.g. a bone scraping against the cartilage, or with respect to the loads and tensions which occur in the joint.

Such joint information relating to motions of the joint can be of a versatile nature. In addition to the physical conditions in the joint itself—i.e. force distributions, tension distributions, touches or irregularities in the motion—the effects on the surrounding tissue, e.g. pressure being exerted on a nerve, can also be examined using the image data records.

In order to obtain a complete set of image data records for a motion, the greatest possible freedom of movement for the patient is required in the receptacle area of the corresponding imaging device. However, this is problematic in many types of imaging devices, particularly in magnetic resonance scanners. There the patient receptacle is usually a relatively narrow tube, for example having a diameter of 60 or 70 cm, in which it is usually only possible to actually record a very small section of such a motion as a result of the cramped spatial conditions. In order to solve this problem, the use of horseshoe-shaped magnets was proposed; however, such systems are more complicated, more expensive and generally do not supply the desired image quality.

SUMMARY

At least one embodiment of the invention is directed to a method by which even one or very few image data records of a region of the patient comprising the joint can be satisfactorily evaluated with respect to motions.

In at least one embodiment, a method includes
 at least one image data record of the region is first of all recorded,
 the image data record is segmented with respect to at least one mechanically relevant component of the joint in order to determine segmentation information,
 a patient movement model is generated on the basis of the segmentation information and/or the patient movement model is selected from a database of movement models, and
 joint information relating to the motions of the joint is determined from the patient movement model.

Accordingly, according to at least one embodiment of the invention, it completely suffices to record only one or very few three-dimensional image data records which cover a small part of the motion or motions in order to nevertheless obtain physical and physiological joint information which can in a later, subsequent step be utilized in particular for the diagnosis. To this end, it is ultimately proposed that the image data record is segmented with respect to the mechanically relevant components of the joint, that is to say the three-dimensional position and size of at least part of the components of the joint determining the motions is determined. The segmentation information obtained in this case can, in particular in magnetic resonance imaging, for example comprise information relating to different body tissue types, e.g. relating to bones, cartilage, muscles, tendons, nerves, fat, skin, etc. It follows that anatomical segmentation information is obtained from the three-dimensional image data record; however, it is also possible for molecular biological data to be collected, particularly when using magnetic resonance.

The segmentation information, which thus comprises the anatomical position, size and possibly further information regarding mechanically relevant components of the joint, is used to generate a patient movement model or to select the latter from a database. The patient movement model is a mechanical model which at least covers the examined region. In addition to the position, in particular the relative position, size and orientation of relevant components in the region, it also comprises further properties which are assigned to the various components and which define the movement properties of the latter.

In particular, provision can be made in this case for biomechanical parameters, in particular elasticity moduli and/or torsional moduli and/or shear moduli, to be assigned to the segmented components in the patient model. These biomechanical parameters can be obtained from measurements on the patient; however, they can additionally, or alternatively, be obtained from the database and/or a parameter database.

Based on this basic information, it is now possible according to at least one embodiment of the invention for the joint information relating to the motions of the joint to be determined using the patient movement model. Simulation techniques, as are widely known from the field of physics, form the basis for this determination. The finite element method (FEM) is an example of such a simulation technique. However, in principle it is also feasible not only to use simulations to determine the joint information, but also to carry out calculations on the basis of physical connections. The advantage of such a patient movement model is that, in that case, not only can joint information relating to motions which go beyond the recorded data record or records be obtained, but, for example, it also affords the possibility of observing different motions. It follows that a tool is provided which combines all the physics of the joint in a patient movement model and from which, depending on the question, arbitrary physical information regarding the motions in the joint can be obtained.

Thus, this particularly advantageously makes an examination possible in the case of positions and motions of a body region to be examined which could not be measured in an imaging device, in particular a magnetic resonance scanner, due to lack of space.

In a development of at least one embodiment of the inventive idea, provision can be made for at least two image data records to be recorded, in which boundary contours between different components of the joint are determined in order to determine the segmentation information in a high resolution image data record and in which components of the joint are identified from at least one further image data record. Thus, it is proposed to record at least two three-dimensional image data records for at least one position, one of the image data records being able to display highly-resolved anatomical boundaries, with the other one however being able to distinguish in particular between different tissue types; this in general is detrimental to the resolution of the boundary regions. This affords the possibility of reliably determining both the position and the type of tissue. In principle, it is of course also possible for the method according to the invention to be carried out using only one image data record per position; however, in this case a suitable compromise has to be found between the resolution on the one hand and the ability to distinguish between tissue types on the other.

As mentioned above, according to at least one embodiment of the invention there are two basic options for generating a suitable patient movement model. Whereas, on the one hand, it is possible for a model to be generated only on the basis of the segmentation information and possibly on the basis of biomechanical parameters from measurements or a parameter database—although more information is usually required in this case—according to the invention, it is preferred if a database of movement models is drawn upon. In this database, very different movement models for the region are "mounted" for different geometries in the style of an atlas, which movement models were particularly advantageously derived from earlier examinations of different patients, i.e. they represent real conditions.

Preferably, these movement models stored in the database have already been "calculated", that is to say joint information is already available in them, for example typical movement curves and force and tension distributions occurring in this case. Hence, these previously carried out simulations and calculations are already stored in the movement models of the patient database.

The database can also be used in different advantageous ways. However, in all cases, provision is first of all made for a movement model in the database to be determined which has the best correspondence with the image data record, i.e. ultimately with the segmentation information. This determination is generally effected by comparison, with it being possible for e.g. a similarity measure to be calculated. This closest movement model from the database can now be used directly as a patient movement model, which will be discussed in more detail in the following text, or it can, if a new patient movement model was generated, be used to adapt the latter.

Thus, in the case of a newly generated patient movement model, provision can be made for a closest database movement model to be determined in a database by comparison and the patient movement model is complemented by transferring information which is missing in the patient movement model from the database movement model. That is to say if information which is required to determine joint information is still missing in this newly generated patient movement model, the information can be added by using the database.

In an alternative refinement, as discussed above, provision can be made for a movement model to be selected as a patient movement model from the database which corresponds closest to the anatomy of the patient with respect to the segmentation information. Thus, in this case, a new patient movement model is not necessarily generated, but one is first of all taken from the database. However, this model need not yet necessarily optimally correspond to the real patient and so it is nevertheless possible to use the information from the image data record, which is of course more precise with respect to the patient, by adapting the patient movement model selected from the database by using the segmentation information. That is to say the movement model from the database as a patient movement model is adapted such that positions determined therein correspond as precisely as possible to the segmentation information from the measured image data record. That is to say optimal correspondence with the measured data is intended to be achieved.

If a number of positions of the joint were covered by image data records, provision can also be made for movement curves in or from the patient movement model to be determined from the database, which movement curves are then fitted to the measured positions. Incidentally, it is already possible here to extrapolate movement curves for positions which were not measured. Reference is made to the fact that it is also feasible for an adaptation of previously calculated or previously simulated data, e.g. force or tension distributions, stored in the movement model in the database to be undertaken on the basis of the comparison with the segmentation information. Then a new calculation is no longer necessary.

In general, for further improvement of the patient movement model, provision can be made for at least one second position of the joint being determined by simulation during the generation of the patient movement model or during the selection of the patient movement model from the database on the basis of the segmentation information of at least one image data record displaying at least one first position of the joint and the at least one second position being compared to the segmentation information of at least one further image data record displaying at least one second position, with the patient movement model being adapted if the patient movement model deviates from the image data record. This means that it is possible for the patient movement model to be improved in a so-to-speak iterative manner by using further image data records which correspond to different positions of the joint than those on which the generation or selection is based, and comparing the further image data records to calculated or simulated positions in the patient movement model. An adaptation can then be effected depending on the result of the comparison. The at least one additional image data record can be recorded after the generation or selection of the patient movement model in a renewed measurement, but already recorded image data records of further positions can first of all be held back so as to be used later within the scope of this optimization process. The quality of the patient movement model can also be assessed depending on the result of the comparison.

In a particularly expedient refinement of at least one embodiment of the present invention, provision can be made for the user to define at least one motion, in particular in a manipulatable anatomical chart of the patient movement model and/or by selecting typical motions, in order to determine the joint information and the joint information is determined by simulation, using the finite element method in particular, of the motion and/or on the basis of data of previously carried out simulations and/or calculations stored in the database. That is to say a user must first of all define which motions are even relevant and which joint information relating to this is even required. This can be effected from a list which is e.g. predetermined, but it is particularly advantageous for a manipulatable anatomical chart of the model to be provided in which new positions and the motion thereto can be defined directly. A suitable display device, e.g. a monitor, therefore displays an in particular three-dimensional image of the region, in particular of the joint and the moveable components thereof.

This illustration can be abstract, but can also be based on the image data record. By way of example, by clicking with a mouse or another input means, in particular a three-dimensional input means, the user can now select moveable parts of the joint and move the latter in possible directions, as a result of which, in particular, a motion to a further position is defined. (Ideally, the initial position is one of the recorded positions). If adapted or original data from previously performed simulations and/or calculations are already available in the patient movement model, the required information can be determined directly and be displayed. If no data is available yet for the selected motion, this data can be determined online or offline, in particular by simulation, and can then possibly be displayed.

A combination of the two procedures is also feasible. Reference is made at this point to the fact that it is of course also possible, in principle, for the entire model to be calculated before such precise questions are posed, i.e. for data to be collected for all possible positions and/or motions. By way of example, this can be effected by a relatively long online or offline simulation. In any case, it is all the more advantageous the faster the data and, in particular, the joint information desired by the user is available because these can then be displayed directly, where possible in real time, as a reaction to an undertaken manipulation of the display.

Provision can expediently be made for the joint information to be displayed in an anatomical or the anatomical chart of the patient movement model, in particular by coloring and/or superposition. If forces and/or tensions in at least one position and/or for at least one motion are determined as joint information, these can for example be superposed in a color-coded fashion on an anatomical chart of the patient movement model; in particular, it is possible for a corresponding color adjustment to be effected directly as a reaction to the manipulation if an illustration is present which can be interpolated. In this fashion, the joint information is also displayed particularly neatly.

In addition to the joint information, it is also possible for specific attributes of the movement model to be displayed, in particular specific attributes stored in a movement model selected from the database. By way of example, such specific attributes can be malalignments in the joint or the like, which in principle are already known, especially if a movement model is selected from a database, and which can provide the user with important further indications for a conclusive diagnosis. Such specific physical attributes can, for example, be displayed as text overlays or red markings of certain regions.

In a further advantageous refinement of the method according to at least one embodiment of the invention, provision can be made for the newly generated and/or adapted patient movement model to be stored in the database. In this fashion the database is extended in each examination by a further movement model and so, in end effect, a comprehensive database is generated which achieves wide coverage of all possible cases.

BRIEF DESCRIPTION OF THE DRAWINGS

Further advantages and details of the present invention emerge from the example embodiments described below and from the drawing.

Here the only FIGURE shows a sketch of the procedure of the method according to an embodiment of the invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The figure shows in an overview the procedure and the functioning of an example embodiment of the method according to the invention. First of all, at least one magnetic resonance data record of a region of the patient comprising a joint, in this example a hip joint, is recorded in step 1. In the process, a number of magnetic resonance data records are obtained in the present case, specifically those for two first positions of the hip joint which are possible in the narrow space within the patient receptacle of the magnetic resonance scanner. For each of these two first positions, a highly resolved magnetic resonance data record, in which the boundaries of components of the hip joint can clearly be seen, and a further magnetic resonance data record, in which different tissue types can be distinguished particularly well, are recorded.

In step 1, the magnetic resonance data records are also segmented in order to obtain segmentation information regarding the recognizable components of the joint, with the position and the dimensions, that is to say in particular all necessary data of the bones, the cartilage, the muscles, the tendons, the nerves, the fat, and the skin, being determined from the three-dimensional magnetic resonance data in the present case. Segmentation techniques for determining such segmentation information are widely known in the prior art and need not be discussed in any more detail here. The magnetic resonance data records together with the segmentation information form the measured data 2.

Additionally, provision is now also made for a database with a multiplicity of movement models of very different patients. The movement models stored in the database already contain results of previously carried out simulations and calculations of motions and possibilities in the joint as data as well, in addition to the anatomical arrangement information regarding the components of the joint.

The database 3 also contains information regarding the biomechanical parameters, that is to say e.g. elasticity moduli, torsional moduli and shear moduli of the relevant components of the joint, which can then be assigned to the former in the movement model. Of course, it is also feasible for these parameters to be measured on the patient in a targeted fashion or to be obtained from an additional parameter database (not illustrated here).

As indicated by the arrows 4, both the database 3 and the measured data 2 are now used to obtain a patient movement model in a step 5. Although in principle it is also feasible for a patient movement model to be newly generated from the measured data 2 alone, in particular by using the segmentation information, and then for the model to be complemented on the basis of e.g. similar models in the database 3, the exemplary embodiment illustrated here, which does not restrict the invention, considers the case where a movement model which fits the segmentation information best is selected from the database 3 as a patient movement model. By way of example, this can be effected by a comparison on the basis of a similarity measure. The most similar movement model from the database 3 is then first of all assumed to be the patient movement model. However, in order to improve the patient movement model selected in this fashion for the individual patient, an adaptation of the patient movement model is provided for in step 6.

First of all, the patient movement model is adapted such that it corresponds, as optimally as possible, to the measured data 2 comprising the segmentation information. However, another additional improvement step is provided for in the present case. This is because a second position which can nevertheless be recorded in the magnetic resonance scanner is simulated or calculated in the patient movement model, and the result is compared to additional magnetic resonance data records of the patient which show the joint in this second position. Firstly, the comparison result serves as verification, that is to say for assessing the quality of the patient movement model, but it can also be used to further adapt the latter.

At this point, reference is made to the fact that adapting already available data regarding positions and motions, e.g. the previously calculated and/or simulated data, can be adapted within the scope of the adaptation process in step 6.

In an optionally indicated step 7, all or still missing data regarding the possible motions and positions of the joint in the patient movement model can now first of all be simulated and/or calculated in advance. Here a finite element method (FEM) can advantageously be used, as is the case, in particular, in all simulations mentioned here. The advantage of such an advance calculation and/or transferring data from the movement model in the database lies in the fact that then it is not necessary for these partly complex calculations to be carried out later.

In particular, in addition to the positions, shapes and orientations of the relevant components of the joint, it is also possible for force and tension distributions, typical movement curves and the like to be determined in the process. It is also possible for singular effects—e.g. touching between components—to be determined in advance.

Finally, an anatomical chart of the patient movement model is displayed in a step 8. It follows that the hip joint of the patient is displayed to the user in three dimensions, with the initial position ideally being one of the recorded positions. Furthermore, the user now also has at least one input device which the user can use to manipulate the display in a fashion which is also possible in the actual joint. For example, a three-dimensional mouse can be used to select a moveable element, in particular a bone, and move the latter in possible directions. If the data relating to the effected motion and the new position is already available, or if it is possible for the latter to be calculated quickly online, c.f. optional step 7, the desired joint information can be displayed immediately, i.e. the display of the desired information is carried along online. This is illustrated by the arrow 10 leading back to step 8 from step 9 relating to the manipulation and possibly to the calculation or simulation.

By way of example, provision can be made for the force or tension distributions in the joint to be superposed on the display in a color-coded fashion and so a check can immediately be carried out as to what effects a given movement has. Other information, e.g. singularly-occurring events or physical variables which are difficult to illustrate graphically, e.g. frictional energies or the like, can be illustrated additionally, e.g. as text. It is also possible for specific attributes of the patient movement model, e.g. malalignments or the like, to be displayed as well.

Once the examination and determination and display of the physical parameters of the joint are finally completed by repeating steps 8 and 9, a diagnosis can finally be effected in a step 11 which is not included in the method according to an embodiment of the invention.

Once the process is complete, the patient movement model is stored in the database 3 and so the latter is extended by this individual case and the information is placed on a broader base.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for evaluating at least one image data record of a region of a patient including at least one joint by a computer device, that the method comprising:
    recording the at least one image data record of the region;
    segmenting, by the computer device, the recorded at least one image data record with respect to at least one mechanically relevant component of the joint in order to determine segmentation information;
    at least one of
        generating, by the computer device, a patient movement model based upon the determined segmentation information, wherein a closest database movement model is determined by comparison with a database including a plurality of different movement models and wherein the patient movement model is complemented by transferring information, missing in the patient movement model, from the database movement model, and
        selecting, by the computer device, the patient movement model from a database of movement models, wherein a closest corresponding movement model is selected from the database with respect to the segmentation information of the anatomy of the patient as the patient movement model;
    determining, by the computer device, joint information relating to the motions of the joint from the at least one of the generated and selected patient movement model, the joint information providing motions of the joint missing from the patient movement model by extrapolating mechanical movement curves of the joint for positions within a range of mechanical motion of the joint which were not recorded;
    determining, by the computer device, at least one second position of the joint through simulation during the generation of the patient movement model or during the selection of the patient movement model;
    comparing at least one first position of the joint and the at least one second position to the segmentation information of at least one further image data record;
    modifying the patient movement model that is stored in the database of movement models if the comparing indicates that the patient movement model deviates from the image data record, the adapted patient movement model that is stored being an improved representation of the segmentation information utilized in a later simulation to determine the second position of the joint; and generating an anatomical chart, on a display device, the anatomical chart illustrating the joint and being interactive such that a user can vary the displayed joint through the mechanical movement curve of the joint including the motions determined through extrapolation.

2. The method as claimed in claim 1, wherein at least two image data records are recorded, in which boundary contours between different components of the joint are determined in order to determine the segmentation information in a high resolution image data record and wherein components of the joint are identified from at least one further image data record.

3. The method as claimed in claim 2, wherein biomechanical parameters are assigned to the segmented components in the patient model.

4. The method as claimed in claim 3, wherein the biomechanical parameters are determined from measurements at least one of on the patient, from the database and from a parameter database.

5. The method as claimed in claim 1, wherein biomechanical parameters are assigned to the segmented components in the patient model.

6. The method as claimed in claim 5, wherein the biomechanical parameters are determined from measurements at least one of on the patient, from the database and from a parameter database.

7. The method as claimed in claim 5, wherein the biomechanical parameters include at least one of elasticity moduli, torsional moduli, and shear moduli.

8. The method as claimed in claim 7, wherein the biomechanical parameters include at least one of elasticity moduli, torsional moduli, and shear moduli.

9. The method as claimed in claim 1, wherein the patient movement model selected from the database is adapted on the basis of the segmentation information.

10. The method as claimed in claim 1, wherein the user defines at least one motion in order to determine the joint information and the joint information is determined at least one of by simulation of the motion, on the basis of data of previously carried out simulations and on the basis of calculations stored in the database.

11. The method as claimed in claim 10, wherein the user defines at least one motion at least one of in a manipulatable anatomical chart of the patient movement model and by selecting typical motions.

12. The method as claimed in claim 1, wherein at least one of forces and tensions, at least one of in at least one position and for at least one motion, are determined as joint information.

13. The method as claimed in claim 1, wherein the joint information is displayed in an anatomical or the anatomical chart of the patient movement model.

14. The method as claimed in claim 13, wherein specific physical attributes of the patient movement model are also displayed.

15. The method as claimed in claim 13, wherein the joint information is displayed in an anatomical or the anatomical chart of the patient movement model by at least one of coloring and superposition.

16. The method as claimed in claim 14, wherein specific attributes stored in a movement model selected from the database are also displayed.

17. The method as claimed in claim 1, wherein the at least one of newly generated and adapted patient movement model is stored in the database.

18. The method as claimed in claim 1, wherein the at least one image data record is at least one magnetic resonance image data record.

19. A non-transitory computer readable medium including program segments for, when executed on a computer device, causing the computer device to implement the method of claim 1.

* * * * *